(12) United States Patent
Yogun et al.

(10) Patent No.: US 7,773,835 B2
(45) Date of Patent: Aug. 10, 2010

(54) COATING MATERIAL AND FIBER OPTIC SENSOR IN WHICH THIS COATING MATERIAL IS USED

(75) Inventors: Halime Usta Yogun, Istanbul (TR); Yavuz Ercil, Istanbul (TR); Yusuf Menceloglu, Istanbul (TR); Naci Inci, Istanbul (TR)

(73) Assignee: Arcelik Anonim Sirketi, Istanbul (TR)

( * ) Notice: Subject to any disclaimer, the term of this patent is extended or adjusted under 35 U.S.C. 154(b) by 27 days.

(21) Appl. No.: 11/572,419

(22) PCT Filed: Jul. 19, 2005

(86) PCT No.: PCT/IB2005/052397

§ 371 (c)(1),
(2), (4) Date: Nov. 21, 2007

(87) PCT Pub. No.: WO2006/011117

PCT Pub. Date: Feb. 2, 2006

(65) Prior Publication Data

US 2008/0240667 A1   Oct. 2, 2008

(30) Foreign Application Priority Data

Jul. 23, 2004 (TR) .......................... A 2004 01827

(51) Int. Cl.
*G02B 6/00* (2006.01)
(52) U.S. Cl. ......................................................... 385/12
(58) Field of Classification Search ................... 385/12, 385/13
See application file for complete search history.

(56) References Cited

U.S. PATENT DOCUMENTS

| 3,894,992 A | | 7/1975 | Raynolds et al. |
| 5,109,442 A | | 4/1992 | Klainer et al. |
| 5,119,463 A | * | 6/1992 | Vurek et al. ................. 385/129 |
| 5,326,531 A | * | 7/1994 | Hahn et al. .............. 422/82.06 |
| 5,882,936 A | * | 3/1999 | Bentsen et al. ................ 436/68 |
| 6,342,295 B1 | | 1/2002 | Kobayashi |
| 6,428,717 B1 | | 8/2002 | Sakai et al. |
| 7,119,137 B2 | * | 10/2006 | Darlington et al. .......... 524/445 |

FOREIGN PATENT DOCUMENTS

| DE | 10056771 A1 | 10/2001 |
| EP | 0601816 A | 6/1994 |
| EP | 0606174 A | 7/1994 |
| JP | 61201143 A | 9/1986 |
| JP | 06094623 A | 4/1994 |
| JP | 2003270141 A | 9/2003 |

* cited by examiner

*Primary Examiner*—Charlie Peng
(74) *Attorney, Agent, or Firm*—Venable, Campillo, Logan & Meaney, P.C.

(57) ABSTRACT

This invention relates to a coating material that is applied on organic and/or inorganic surfaces and that can detain moisture and easily release the moisture that is detained after a certain time, and a fiber optic sensor (1) where this coating is utilized.

15 Claims, 1 Drawing Sheet

[Fig. 001]
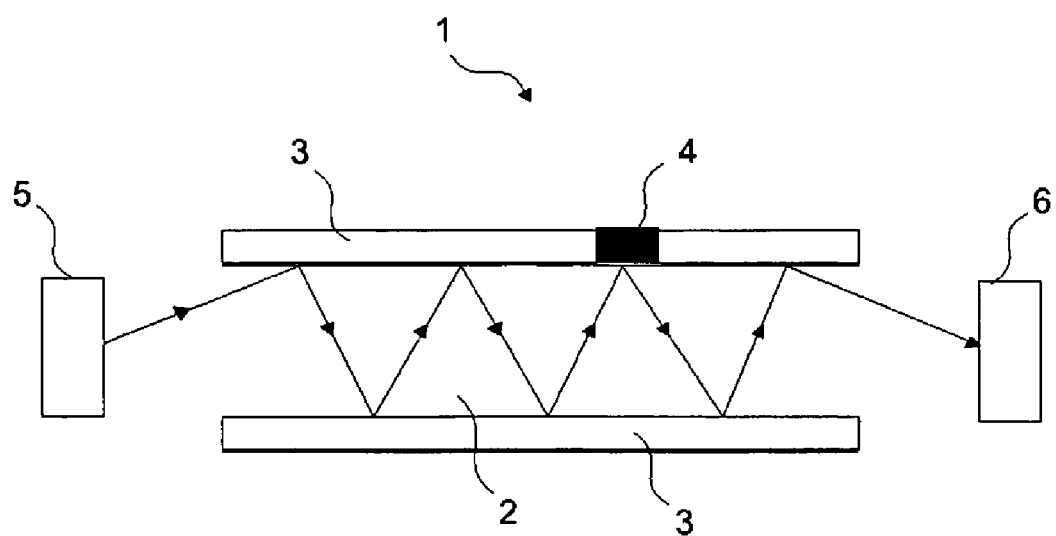

COATING MATERIAL AND FIBER OPTIC SENSOR IN WHICH THIS COATING MATERIAL IS USED

This invention relates to a coating material that is applied on organic and/or inorganic surfaces and to a fiber optic sensor where this coating material is used.

Polyethylene Glycol (PEG) has a very high hydrophilic (likes water) property, detaining moisture. For this reason, its usage is well known especially for moisture sensor applications. However, certain problems are experienced when sensor material particularly Polyethylene Glycol (PEG) is to be coated on surfaces of glass or plastic fiber optic materials. Especially for fiber optic moisture sensors, PEG material that is applied as moisture sensitive sensor material, can not release the moisture content that it has detained at high moisture levels; thus, adversely affecting the repeatability and linearity of the data that the moisture sensor detects.

In the current state of art, U.S. Pat. No. 5,109,442 describes a fiber optic sensor structure which repels water from its surface and which includes long, hydrophobic (dislikes water) chained polymeric silanes. Polymeric silanes have general structures where alkyltrialkoxysilanes or octadecyltrimethoxysilanes are used.

The object of this invention is to realize a coating material that is applied on organic and/or inorganic surfaces and that can detain moisture and easily release the moisture that is detained after a certain time.

One other object of the present invention is to realize a fiber optic sensor on which a sensor manufactured with the use of a coating material is coated.

The fiber optic sensor where this coating material is used designed to fulfill the objectives of the present invention is illustrated in the attached figures, where:

FIG. 1—is a schematic view of a fiber optic sensor. Parts shown in figures are numbered as follows:
1. Fiber optic sensor
2. Core
3. Cladding
4. Detector
5. Transmitter
6. Receiver Coating material that is the object of the present invention is applied to fiber optic sensors (1) which are particularly affected by moisture level deviations, and which sense moisture levels.

Coating material that is the object of the present invention comprises a hydrophilic material that has a property to attract moisture that is applied on organic or inorganic surfaces and a hydrophobic material that avoids the detaining and releasing mechanisms of the moisture content with a hydrophilic material that attracts moisture and the accumulation of excessive moisture molecules inside the hydrophilic material, that simplifies and organizes the release of water molecules settled inside the hydrophilic material in the shortest time when moisture concentration decreases, and that has a property of repelling moisture.

As hydrophilic material, olygomer and/or polymer materials that are sensitive to various chemicals of hydroxyl, amino, thiol or carboxyl may be used. For the preferred application of the invention polyethylene glycol (PEG) which has a property to detain moisture is utilized as a hydrophilic material.

As hydrophobic material; on the other hand, materials that comprise perfluoroalcohol (PFA) group which is known to have a hydrophobic and moisture repelling property are used. For the preferred application of the invention, preferably perfluoroalchiletylalcohol is used as perfluoroalcohol.

Coating material comprises a binding agent that increases the grip of the hydrophilic and hydrophobic material to the surface to be coated. The binding agent has an adhering effect and as a binding agent trialcoxy silane group preferably gamma-isocyanatopropyltriethoxysilane, is applied.

When hydrophilic material is prepared, moisture content of the PEG material is removed with the dean-stark distillation inside toluene solvent methodology. PEG and toluene solution, from which moisture content is removed, is processed with gamma-isocyanatopropyltriethoxysilane as the binding agent with adhesive effect. During this process, hydroxyl (OH) groups with hydroxyl ends in PEG material react with gamma-isocyanatopropyltriethoxysilane, one of the trialcoxy silane groups used as a binding agent, and after this reaction trialcoxy silane groups bind with a urethane bond to the ends of PEG chains. By binding PEG and gamma-isocyanatopropyltriethoxysilane, hydrophilic material and binding agent mix that has an end group of trialcoxy silane is obtained. The general formula of the hydrophilic material, the compound of PEG with trialcoxy silane coated end groups formed after the reaction of PEG and gamma-isocyanatopropyltriethoxtysilane, being the object of the present invention, is as follows:

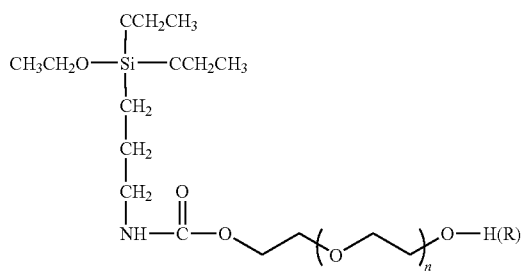

When hydrophobic material is prepared, PFA and gamma-isocyanatopropyltriethoxysilane used as a binding agent are processed with the use of a solvent. The solution is mixed by the addition of a catalyst, tin (II) 2-ethylhexanoate, to the solution obtained at the end of this process. The general formula of the hydrophobic material and the binding agent is given as follows:

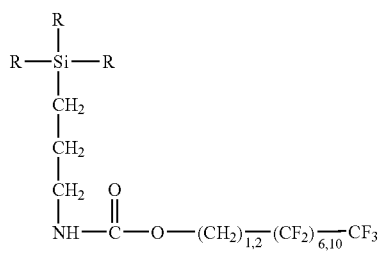

Coating material is obtained by dissolving and/or dispersing the hydrophilic and hydrophobic material and binding agent mixture in water with certain proportions and different concentrations. For example:

In one of the preferred applications of the invention, 3.75 mmol PEG material with a hydroxyl end is dissolved in 180 ml toluene solvent. This solution is processed with dean-stark distillation method for 3 hours and moisture content that is trapped inside the PEG material is removed from the material. PEG and toluene solution, with the moisture removed from its content, is processed with 7.5 mmol gamma-isocyanatopropyltriethoxysilane for a certain period at approximately 50°C; hence, the hydrophilic material and binding agent mixture is obtained. In addition, PFA, particularly 6 g perfluoroalkylethylalcohol, and 3.41 g gamma-isocyanatopropyltriethoxysilane that is used as a binding agent is dissolved in 42 ml tetrahydrofuran solvent. Tin (II) 2-ethylhexanoate is included in this solution as a catalyst and the solution is mixed. At the end of this process PFA reacts with one of the trialcoxy silane groups, gamma-isocyanatopropyltriethoxysilane, which is used as a binding agent and as a result of this reaction trialkoxy silane groups bind with urethane bonds to the ends of PFA chains. By combining PFA and gamma-isocyanatopropyltriethoxysilane, a mixture of hydrophobic material and binding agent is obtained. Additionally, by combining the hydrophilic material, hydrophobic material and binding agent mixture, coating material is obtained.

It is possible to coat the material on organic and/or inorganic surfaces such as PMMA materials from which fiber optic sensors (1) are manufactured. Coating material can also be applied on silica glass material.

The fiber optic sensor (1) where the coating material that is the subject of invention is used comprises a core (2) that is used as a light transmission line and that is preferably manufactured from plastic fiber optic material, a cladding (3) which thoroughly surrounds the core (2) and has a lower refractive index than the refractive index of the core (2) and is preferably manufactured from a plastic fiber optic material, a detector (4) manufactured from the coating material that is coated on organic or inorganic surfaces, a monochromatic transmitter (5) that is used as a light source and a receiver (6) that senses light.

In the fiber optic sensor (1), a core (2) which is preferably manufactured from PMMA material is used. The part of the cladding (3) which thoroughly surrounds the core (2) is partially or completely scratched just up to the surface of the core (2) with various methods; thus, the part that will be coated with the detector (4) is revealed. The detector (4) manufactured from the coating material that includes hydrophilic and hydrophobic material is easily coated permanently to this part that is formed by scratching the cladding (3), creating a cross bond on PMMA material. Detector (4) is coated preferably with dip coating method.

Light that is transmitted into the core (2) from the preferably mono-chromatic transmitter (5) that is used as a light source can not leave the core (2) since the refractive index of the cladding (3) that surround the core (2) is lower than the refractive index of the core (2); hence, is reflected from the cladding (3) and is transmitted inside the core (2). During this transmission light travels as it is reflected from the detector (4).

Moisture content of the medium is detained due to the hydrophilic material present in the coating material of the detector (4) when the fiber optic sensor (1) is situated in the medium that it is to be used. However, as a hydrophilic material PEG detains too much moisture; hence, although the moisture level of the medium decreases PEG can not release this excessive moisture content. Moreover, optical sensitivity of the detector (4) of the fiber optic sensor (1), which is bonded as a cross-bond on PMMA and which is affected from hydrophilic material, can not produce a linear output due to this excessive moisture content. For this reason, coating material is prepared with hydrophilic materials and hydrophobic materials. Hydrophobic material avoids the detaining and releasing mechanisms of the moisture content of a hydrophilic material and the accumulation of excess moisture molecules inside the hydrophilic material, and simplifies and organizes the release of water molecules that settle inside the hydrophilic material in the shortest time when moisture concentration decreases, and that has a property of repelling moisture. Therefore, the linearity and repeatability of the output of the detector (4) is established; hence, sensitivity is enhanced.

When the moisture concentration of the media where the fiber optic sensor (1) is located deviates, optical properties of the detector material; hence, its refractive index deviates which results in the increase or decrease in the amount of light that is transmitted inside the core (2) and the moisture concentration of the media can be computed according to the amount of light that can be transmitted from the core (2) of the fiber optic.

By the application of the coating material that is the object of the present invention, the detector (4) is glued on organic/inorganic surfaces for long periods and a fiber optic sensor (1) with repeatable fiber optic sensor (1) measurement and increased dynamic range and sensing susceptibility is obtained.

The invention claimed is:

1. A coating material that is applied to a surface and is used in fiber optic sensors that can sense moisture levels comprising:
   a hydrophilic material that is affected by moisture level deviations;
   a hydrophobic material that avoids the detaining and releasing mechanisms of the moisture content of the hydrophilic material; and
   wherein the hydrophilic material and the hydrophobic material are combined in a manner so that the hydrophobic material avoids accumulation of excess moisture molecules inside the hydrophilic material; the hydrophobic material simplifies and organizes release of water molecules that settle inside the hydrophilic material in the shortest time when moisture concentration decreases, and repels moisture; and
   wherein the surface is inorganic or organic and the coating material has a property to attract moisture.

2. A coating material as described in claim 1, wherein the hydrophilic material that comprises Polyethyleneglycol (PEG).

3. A coating material as described in claim 1, wherein the hydrophobic material that comprises Perfluoroalkol (PFA) group.

4. A coating material as described in claim 3, wherein the hydrophobic material that comprises perfluoroalcilethylalcohol as PFA.

5. The coating material that is applied to a surface and is used in fiber optic sensors that can sense moisture levels as in claim 1, further comprising:
   a binding agent that increases the grip of hydrophobic and hydrophilic material on the surface to be coated.

6. A fiber optic sensor (1) comprising a core (2) that is used as a light transmission line, a cladding (3) which thoroughly surrounds the core (2) and has a lower refractive index than the refractive index of the core (2), a monochromatic (5) transmitter that is used as a light source and a receiver (6) that senses light, and a detector (4) having a coating material on the cladding (3) after the partial or complete scratching of the cladding (3), wherein the coating material comprises a hydrophilic material processed using a binding agent comprising a trialcoxy silane group; a hydrophobic material processed using the binding agent comprising the trialcoxy silane group; wherein the binding agent increases the grip of hydrophobic material and hydrophilic material on the cladding (3) after the partial or complete scratching of the cladding (3).

7. The fiber optic sensor as described in claim 6, wherein the hydrophilic material comprises Polyethyleneglycol (PEG).

8. The fiber optic sensor as described in claim 6, wherein the hydrophobic material comprises Perfluoroalkol (PFA) group.

9. The fiber optic sensor as described in claim 8, wherein the hydrophobic material comprises perfluoroalcilethylalcohol as PFA.

10. The fiber optic sensor as described in claim 6 or 7, wherein the binding agent is gamma-isocyanatopropyltriethoxysilane.

11. A coating material that can be applied on a surface and that can sense moisture levels comprising: a hydrophilic material processed using a binding agent comprising a trialcoxy silane group; a hydrophobic material processed using the binding agent comprising the trialcoxy silane group; wherein the binding agent increases the grip of hydrophobic material and hydrophilic material on the surface to be coated.

12. A coating material as described in claim 11, wherein the hydrophilic material comprises Polyethyleneglycol (PEG).

13. A coating material as described in claim 11, wherein the hydrophobic material comprises Perfluoroalkol (PFA) group.

14. A coating material as described in claim 13, wherein the hydrophobic material comprises perfluoroalcilethylalcohol as PFA.

15. A coating material as described in claim 12 or 13, wherein the binding agent is gamma-isocyanatopropyltriethoxysilane.

* * * * *